United States Patent [19]

Shimuzu et al.

[11] Patent Number: 5,679,372
[45] Date of Patent: Oct. 21, 1997

[54] ABSORBABLE TOPICAL HEMOSTAT

[75] Inventors: Yasuhiko Shimuzu, Uji; Toru Natsume; Toshikazu Makihara, both of Tsukuba; Masanori Akasaka, Nagoya; Hiroki Sakakibara, Tokyo, all of Japan

[73] Assignees: Yasuhiko Shimizu, Kyoto; Nippon Meat Packers, Inc., Osaka; Mitsubishi Chemical Corporation, Tokyo, all of Japan

[21] Appl. No.: 424,414

[22] PCT Filed: Nov. 2, 1993

[86] PCT No.: PCT/JP93/01587

§ 371 Date: Apr. 26, 1995

§ 102(e) Date: Apr. 26, 1995

[87] PCT Pub. No.: WO94/09831

PCT Pub. Date: May 11, 1994

[30] Foreign Application Priority Data

Nov. 2, 1992 [JP] Japan ................................. 4-294273

[51] Int. Cl.$^6$ .......................... A61L 15/00; A61F 13/00; A61M 35/00
[52] U.S. Cl. .......................... 424/445; 424/443; 424/444; 604/289; 604/290
[58] Field of Search .................. 604/289, 290; 128/296; 424/422, 443–447; 530/356, 399

[56] References Cited

U.S. PATENT DOCUMENTS

| | | | |
|---|---|---|---|
| 4,271,070 | 6/1981 | Miyata et al. | 260/123.7 |
| 4,292,972 | 10/1981 | Pawelchak et al. | 128/296 |
| 4,404,033 | 9/1983 | Steffan | 106/161 |
| 4,565,580 | 1/1986 | Miyata et al. | 106/124 |
| 5,024,841 | 6/1991 | Chu et al. | 424/422 |
| 5,206,028 | 4/1993 | Li | 424/484 |
| 5,512,291 | 4/1996 | Li | 424/443 |

FOREIGN PATENT DOCUMENTS

| | | |
|---|---|---|
| 0 463 887 A2 | 1/1992 | European Pat. Off. . |
| 463887 | 2/1992 | European Pat. Off. . |
| 2-182259 | 7/1990 | Japan . |
| 3-295561 | 12/1991 | Japan . |
| 4-61862 | 2/1992 | Japan . |

OTHER PUBLICATIONS

"A New Collagen Topical Hemostatic Agent–Comparative Evaluation In Experimental Animal Wounds", Jpn Artif Organs 19(3),1235–1238 (1990).

*Primary Examiner*—John G. Weiss
*Assistant Examiner*—David J. Cho
*Attorney, Agent, or Firm*—Frishauf, Holtz, Goodman, Langer & Chick, P.C.

[57] ABSTRACT

An absorbable spun, cotton-like topical hemostat containing fibers entangled with each other and being made of atelcollagen obtained by reconstituting solubilized collagen. Each of the fibers has a diameter of 10 to 70 μm and a length of 3 to 70 mn. At least a part of the collagen molecules constituting the fibers are crosslinked by heat at a temperature of 50° to 200° C. The hemostat is swellable upon contact with blood. In use, the hemostat readily adapts to the shape of the hemorrhagic site, has an adhesiveness to a bleeding surface and provides an effective suppression of hemorrhage.

9 Claims, 2 Drawing Sheets

ABSORBABLE TOPICAL HEMOSTAT

TECHNICAL FIELD

This invention relates to an absorbable topical hemostat comprising a cotton-like product of collagen fibers to be used in the field of surgery, particularly to an absorbable topical hemostat which can be applied rapidly and effectively to hemorrhage from parenchymatous internal organs and capillary hemorrhage.

BACKGROUND ART

As a hemostatic method during a surgical operation, there may be mentioned a compression method, a ligation method, an electrocoagulation method, application of a physiologically active substance such as thrombin, fibrin paste, etc. and others. To an arterial hemorrhage with clear hemorrhagic sites, a ligation method or an electrocoagulation method has generally been applied. In the case of a venous hemorrhage, hemostasis is easily and sufficiently obtained by compression. However, these hemostatic methods are sometimes ineffectual to control a hemorrhage from parenchymatous internal organs and capillary hemorrhage, and when there is a tendency of hemorrhage in hepatic insufficiency or in the field of cardiovascular surgery, hemostasis is particularly difficult. In such a case, an absorbable topical hemostat which accelerates a blood coagulation reaction only by contacting it with a bleeding surface, whereby thrombus is formed rapidly to inhibit hemorrhage, is effective since not only is operation time shortened, but also postoperative rehemorrhage is prevented, to contribute to safe postoperative control. For this purpose, various topical hemostats using oxidized cellulose as a material have been developed and applied clinically. They have advantages that they are inexpensive and have excellent handling property, but they have disadvantages that since they do not use a material derived from an animal body, absorption into a living body is slow, and a strong hemolysis reaction and a reaction rejecting a foreign body are caused. In recent years, topical hemostats using collagen which is protein derived from an animal body have frequently been applied clinically since the collagen has low antigenicity and is absorbed into a living body safely to minimize an allergic reaction and a reaction rejecting a foreign body and further the collagen itself also has physiological functions (coagulation of platelets by adhesion, acceleration of a blood coagulation system by the platelet factor III released from coagulated platelets and formation of thrombus) thus, its hemostatic effect is high.

Topical hemostats made of collagen which have been put to practical use at present include those in which microfibrils of collagen are made flaky and those in which a collagen sponge is made plate-shaped. As to the former, telopeptide which is a determinant of antigenicity of collagen remains to exhibit antigenicity in a living body, so that they are required to be removed after use, they are flaky, so that they are flowed by blood to be scattered, whereby a large hemostatic effect cannot be expected, and they are easily charged with static electricity, so that there is a drawback in handling that they are easily attached to hands and tweezers during use. On the other hand, as to the latter, some of them comprise atelocollagen in which telopeptide has been removed, but they are plate-shaped, so that adhesiveness to a wound surface with a complicated shape is not sufficient and also astriction cannot be carried out, whereby a large hemostatic effect cannot be expected similarly as in the former.

As a material which can solve the above drawbacks, cotton-like topical hemostats comprising atelocollagen have been published. There may be mentioned, for example, a material obtained by spinning atelocollagen derived from porcine skin, drying it and forming it into a cotton-like product (Shimizu et al., Artificial Internal Organs 19 (3), 1235 (1990)), a material obtained by treating spun collagen with a crosslinking agent, washing it and lyophilizing it to be formed into a cotton-like product with a surface on which fine crack-like fissures are made (Japanese Provisional Patent Publication No. 61862/1992), etc. Since the former uses soluble atelocollagen as such, when it is used for hemostasis, it absorbs blood to significantly lower fiber strength, whereby it is difficult to inhibit blood flow and therefore a sufficient hemostatic effect cannot be expected. On the other hand, in the latter, there are problems that since crosslinking treatment with a crosslinking agent is carried out prior to lyophilization, a hemostatic effect possessed by collagen is impaired, and from the point of safety, a washing operation for completely removing an unreacted crosslinking agent is required.

DISCLOSURE OF INVENTION

An object of the present invention is to provide a hemostat in which the tasks of the conventional hemostats made of collagen as described above can be solved, i.e., to provide a topical hemostat made of collagen, which has sufficient hemostatic ability, is degraded in and absorbed into a living body safely and rapidly after use, and also has good handling property.

As a result of investigation for such an object, the present invention has been made.

That is, the present invention is a cotton-like product comprising fibers of atelocollagen obtained by reconstituting solubilized collagen, wherein each of said fibers has a diameter of 10 to 70 μm and a fiber length of 3 to 70 mm, and at least a part of collagen molecules constituting said fibers are crosslinked by heat.

In the present invention, the solubilized collagen refers to collagen subjected to solubilization by carrying out solubilization treatment with protease or a solubilization treatment with alkali and also subjected to an operation of removing telopeptide which is a determinant of antigenicity of collagen. The source of the collagen to be used as a material of the present invention is not particularly limited, but collagen obtained from skin, bone, cartilage, tendon, internal organs, etc. of a mammal (e.g. a human, a cattle, a swine, a rabbit, a sheep, a mouse, etc.) is generally used. Also, collagen-like protein obtained from birds, fish or the like can be used.

In general, collagen subjected to solubilization treatment with protease has a higher activity to platelets as compared with one subjected to solubilization treatment with alkali, so that it is preferred to use collagen subjected to solubilization treatment with protease.

Hemostasis by the collagen hemostat is carried out by physically suppressing sprung blood in the first place and then exhibiting a hemostatic effect of collagen itself. Therefore, in order to make a sufficient hemostatic effect, the strength of fibers constituting the hemostat is an important factor. The strength of the fibers is larger as the diameter of the constituting fibers is larger. However, when the diameter thereof is too large, the fibers become rigid, so that shape processing is difficult. Thus, the diameter may be 10 to 70 μm, preferably 15 to 45 μm.

The length of the fibers can be any desired length since said fibers are obtained by reconstituting solubilized collagen. However, when the length thereof is too long, it is difficult to disperse the fibers sufficiently when said fibers are formed into a cotton-like product, and when the length thereof is too short, the fibers are hardly entangled with each other, so that said fibers are scattered in application of the hemostat and strength resisting blood pressure cannot be obtained. Thus, the length may be 3 to 70 mm, preferably 5 to 50 mm.

The absorbable topical hemostat of the present invention is swollen by absorbing blood to increase the whole volume thereof. As a result, an astriction effect on peripheral tissues of applied sites is exhibited. The astriction effect is exhibited only when the hemostat has a certain degree of strength. In the fibers obtained from the solubilized collagen, a swelling degree thereof is significant, and the strength is lowered accompanied with swelling. Therefore, in the present invention, by crosslinking at least a part of collagen molecules constituting said fibers by heat, suitable swellability (said fibers have a dense surface structure, but they absorb blood rapidly to cause volume expansion, whereby an astriction effect on bleeding sites is brought about) and strength (an action of inhibiting blood stream completely to achieve hemostasis in an early stage) as a hemostat are imparted while maintaining a hemostatic action inherently possessed by collagen.

In the prior art, when collagen is crosslinked, there has been used a method of using a crosslinking agent such as aldehydes, diepoxides, etc. However, in collagen treated by a crosslinking agent, activity to platelets of collagen is lost so that improvement of hemostatic ability cannot be expected (reactivity to platelets of collagen is hardly deactivated by heat treatment). Further, the method of using a crosslinking agent has many problems that the reaction cannot be stopped at the time when crosslinking proceeds to a degree that a swelling degree suitable as a hemostat remains, and the crosslinking agent to be used has toxicity in many cases so that a washing operation for removing unreacted crosslinking agent is required.

The crosslinking treatment by heat is preferably carried out at a range of 50° to 200° C. If it is lower than 50° C., crosslinking becomes insufficient or crosslinking cannot be carried out, while if it exceeds 200° C., denaturation of collagen is remarkable, whereby swellability and physiological activity are lost. When both factors of production and quality are considered, it is more preferably 60° to 180° C., particularly preferably 95° to 150° C.

As another physical property to be possessed by the absorbable topical hemostat, a specific volume of the cotton-like product of collagen fibers is also important in the points of handling property of the hemostat and adhesiveness to wound sites. The specific volume of the fibers is preferably higher from easiness of shape processing in application (the hemostatic effect can be exhibited maximally by changing the shape of the hemostat in accordance with wound sites having various shapes and uniformly adhering it thereto). However, there is a limitation thereof in order to suitably entangle the fibers with each other, and if it is too high, the fibers are scattered or gaps are formed in application, whereby complete hemostasis is difficult. Thus, the specific volume may be 20 to 80 $cm^3/g$, preferably about 40 to 70 $cm^3/g$.

Here, the specific volume is determined as described below (hereinafter, description is made with the cotton-like product of collagen fibers being a standard, but the flake-like product is also measured in the same manner).

① Under standard conditions (20° C., 65% RH), about 1 g of the cotton-like product of collagen fibers obtained is taken and weighed correctly (measured weight: Wg).

② Under the standard conditions, a transparent plastic tube having an inner diameter of 35 mm is uniformly filled with the product.

③ Next, a flat disc having a diameter of 30 mm and a weight of 5.0 g is placed on the cotton-like product prepared in ②, and 50 g of a weight is further placed thereon for 30 seconds. Thereafter, said weight is removed, and the remainder is left to stand for 30 seconds. This operation is repeated three times, and then the height of the filled cotton-like product is measured at three positions in the peripheral direction (the average value is defined as H mm).

④ The specific volumes of three samples are determined according to the following equation, and an average value thereof is used.

Specific volume $(cm^3/g) = ((35/20)^2 \times \pi \times H/10)/W$

BEST MODE FOR CARRYING OUT THE INVENTION

Example 1

Figure 1:
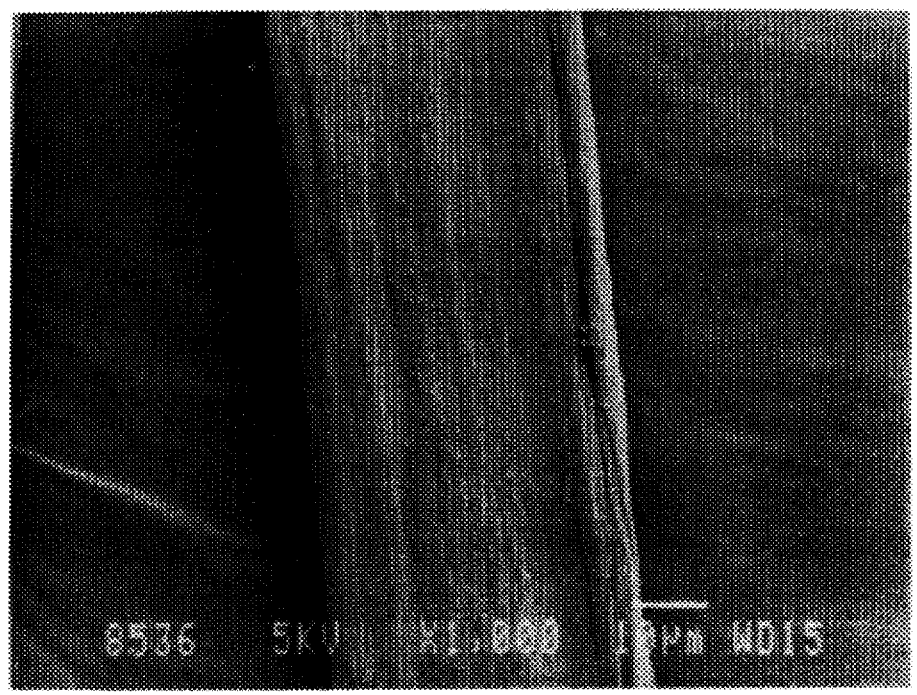
FIG. 1 is a microphotograph (magnification: 1,000) showing a shape of a surface of atelocollagen fiber constituting the absorbable topical hemostat of the present invention.
Figure 2:
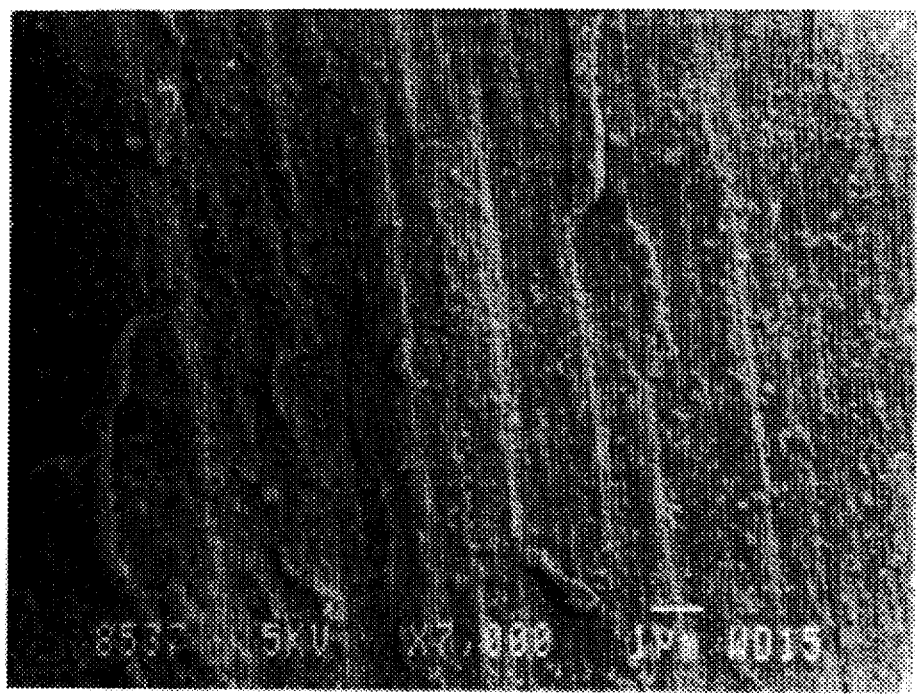
FIG. 2 is a microphotograph (magnification: 7,000) in which said surface is further enlarged.

By treating insoluble collagen obtained from fresh cattle skin with protease (pepsin, hereinafter the same), telopeptide was digested and a solution of solubilized atelocollagen was obtained. Next, this solution was dissolved in an aqueous hydrochloric acid adjusted to pH 2 (collagen concentration: 6%), and atelocollagen fibers were obtained by a wet spinning method using 20% aqueous ammonium sulfate as a coagulating agent. The atelocollagen fibers obtained were desalted and dehydrated with methanol, dried and then cut to have a length of 50 mm. The fibers were dispersed by air blow (at a wind speed of 30 m/s for 10 minutes) and then subjected to heat treatment at 105° C. (for 3 hours) to obtain a cotton-like product of the collagen fibers. The physical property values of the cotton-like product obtained were a fiber length: 5 to 50 mm, a fiber diameter: 15 to 45 μm and a specific volume: 60 $cm^3/g$. The shape of the fiber surface of the cotton-like product obtained is shown in FIG. 1 and FIG. 2 (which are the results of observation by a scanning type electron microscope manufactured by Nihon Denshi Co.: Model JSM-804).

Example 2

A cotton-like product of collagen fibers was obtained in the same manner as in Example 1 except for carrying out the heat treatment at 60° C. (for 24 hours). The physical property values of the cotton-like product obtained were the same as those of Example 1.

Example 3

A cotton-like product of collagen fibers was obtained in the same manner as in Example 1 except for carrying out the heat treatment at 180° C. (for 10 minutes). The physical property values of the cotton-like product obtained were the same as those of Example 1.

Example 4

A cotton-like product of collagen fibers was obtained in the same manner as in Example 1 except for not carrying out the dispersion treatment of the fibers by air blow. The physical property values of the cotton-like product obtained were a fiber length: 30 to 50 mm, a fiber diameter: 15 to 45 μm and a specific volume: 28 cm³/g.

Example 5

A cotton-like product of collagen fibers was obtained in the same manner as in Example 1 except for changing the conditions of the dispersion treatment of the fibers by air blow to a wind speed of 40 m/s for 60 minutes. The physical property values of the cotton-like product obtained were a fiber length: 5 to 50 mm, a fiber diameter: 15 to 45 μm and a specific volume: 78 cm³/g.

Example 6

A cotton-like product of collagen fibers was obtained in the same manner as in Example 1 except for carrying out alkali solubilization treatment (using a mixed solution of sodium sulfate, sodium hydroxide and monomethylamine) in place of the enzyme treatment of insoluble collagen. The physical property values of the cotton-like product obtained were the same as those of Example 1.

Example 7

A cotton-like product of collagen fibers was obtained in the same manner as in Example 1 except for using fresh porcine skin in place of fresh cattle skin. The physical property values of the cotton-like product obtained were the same as those of Example 1.

Comparative Example 1

A cotton-like product of collagen fibers was obtained in the same manner as in Example 1 except for not carrying out the heat treatment. The physical property values of the cotton-like product obtained were the same as those of Example 1.

Comparative Example 2

A cotton-like product of collagen fibers was obtained in the same manner as in Example 1 except for carrying out alkali solubilization treatment (using a mixed solution of sodium sulfate, sodium hydroxide and monomethylamine) in place of the enzyme treatment of insoluble collagen and not carrying out the heat treatment. The physical property values of the cotton-like product obtained were the same as those of Example 1.

Comparative Example 3

A cotton-like product of collagen fibers was obtained in the same manner as in Example 1 except for carrying out treatment with glutaraldehyde in place of the heat treatment. The physical property values of the cotton-like product obtained were the same as those of Example 1.

Comparative Example 4

A cotton-like product of collagen fibers was obtained in the same manner as in Example 1 except for changing the spinning conditions. The physical properties of the cotton-like product obtained were a fiber length: 5 to 50 mm, a fiber diameter: 7 to 9 μm and a specific volume: 65 cm³/g.

Comparative Example 5

A cotton-like product of collagen fibers was obtained in the same manner as in Example 1 except for changing the spinning conditions. The physical properties of the cotton-like product obtained were a fiber length: 5 to 50 mm, a fiber diameter: 80 to 100 μm and a specific volume: 35 cm³/g.

Comparative Example 6

A flake-like product of collagen fibers was obtained in the same manner as in Example 1 except for changing the cut length after drying to 3 mm. The physical property values of the flake-like product obtained were a fiber length: 0.5 to 1 mm, a fiber diameter: 15 to 45 μm and a specific volume: 18 cm³/g.

Comparative Example 7

By treating insoluble collagen obtained from fresh cattle skin with protease, telopeptide was digested and a solution of solubilized atelocollagen was obtained. Next, this solution was dissolved in an aqueous hydrochloric acid adjusted to pH 2 (collagen concentration: 3%), and collagen fibers were obtained by a wet spinning method using a saturated solution of sodium sulfate as a coagulating agent. Next, these fibers were treated with a glutaraldehyde solution and then washed with water to remove inorganic salts and unreacted glutaraldehyde. Next, the fibers were cut to have a length of 50 mm and lyophilized to obtain a cotton-like product of the collagen fibers. The physical properties of the cotton-like product obtained were a fiber length: 40 to 50 mm, a fiber diameter: 10 to 30 μm and a specific volume: 17 cm³/g.

Experiment

Mongrel adult dogs to which 100 u/kg of heparin had been systemically administered before initiation of the experiment were subjected to laparotomy under general anesthesia, and only spleen integument with an exact size of 1 cm×1 cm was peeled off by a surgical knife. Next, each 0.1 g of the collagen cotton-like products and flake-like products obtained in the respective Examples and Comparative examples described above were put on the above peeled surfaces and compressed for 30 seconds, and bleeding amounts were measured at intervals of 1 minute. Dried gauze was put on a bleeding surface for 1 minute, and the bleeding amount was determined by a radius of a circle made by blood absorbed by the gauze. This determination is set forth as an index which is hereinafter referred to as Bleeding Degree: BD. An initial value of BD is defined as $BD_{t=0}$, BD with each lapse of time is defined as $BD_{t=t}$, and a value determined according to the following equation is defined as a hemostatic rate: HR. At the time when no blood permeated into the gauze, hemostasis was regarded to be completed.

$$HR\ (\%) = (1 - (BD_{t=t}/BD_{t=0})) \times 100$$

Data obtained when the respective 10 samples were examined are shown in Table 1. In said table, also shown are results of measuring a time required for processing 0.1 g of the collagen cotton-like products and the flake-like products obtained in the respective Examples and Comparative examples described above in accordance with the shape of the peeled surfaces and applying them to the peeled surfaces (referred to as a reprocessing time).

From the results, it is apparent that the hemostatic collagen cotton-like products of the present invention have excellent hemostatic ability and excellent handling property. In experiment examples of this experiment, in which hemostasis was not completed in an early stage of hemostasis (in 2 minutes), exuded blood was sprung out by partially pushing through the hemostat (because the fibers constituting the hemostat could not maintain strength enough to resist blood pressure), whereby hemostasis was difficult. That is, it is extremely important that hemostasis is completed in 2 minutes.

TABLE 1

| | HR (%) | | | | | Reprocess- |
| | After 1 min | After 2 min | After 3 min | After 4 min | After 5 min | ing time (sec) |
|---|---|---|---|---|---|---|
| Example 1 | 100 | ← | ← | ← | ← | 2 |
| Example 2 | 51 | 100 | ← | ← | ← | 2 |
| Example 3 | 53 | 100 | ← | ← | ← | 2 |
| Example 4 | 75 | 100 | ← | ← | ← | 5 |
| Example 5 | 69 | 100 | ← | ← | ← | 3 |
| Example 6 | 88 | 100 | ← | ← | ← | 2 |
| Example 7 | 100 | ← | ← | ← | ← | 2 |
| Comparative example 1 | 35 | 95 | 63 | 100 | ← | 2 |
| Comparative example 2 | 18 | 24 | ← | ← | ← | 2 |
| Comparative example 3 | 59 | 67 | ← | ← | ← | 3 |
| Comparative example 4 | 31 | 40 | 59 | ← | ← | 3 |
| Comparative example 5 | 36 | 54 | ← | ← | ← | 6 |
| Comparative example 6 | 56 | 86 | ← | ← | ← | impossible |
| Comparative example 7 | 38 | 46 | 62 | ← | ← | 6 |

INDUSTRIAL APPLICABILITY

The cotton-like product of collagen fibers according to the present invention is a gathering of fibers which are obtained by reconstituting solubilized collagen and have suitable length, diameter and specific volume. Since at least a part of collagen molecules constituting said fibers are crosslinked by heat, a suppression effect on hemorrhage which is the first stage of hemostasis is improved, and sufficient hemostatic ability is exhibited without impairing a hemostatic activity inherently possessed by collagen. Also, since it has a suitable specific volume, it can be easily processed in accordance with a shape of a hemorrhagic site, it can be used for hemostasis rapidly, and also adhesiveness to a bleeding surface is good, whereby a hemostatic effect is high.

We claim:

1. An absorbable spun, cotton-like topical hemostat comprising fibers entangled with each other and being made of atelcollagen obtained by reconstituting solubilized collagen, wherein each of said fibers has a diameter of 10 to 70 μm and a fiber length of 3 to 70 mm, and at least a part of collagen molecules constituting said fibers are crosslinked by heat at a temperature of 50° to 200° C., the hemostat being swellable upon contact with blood, the hemostat having a shape which is changeable to conform to a wound site, and the hemostat having a specific volume of 20 to 80 cm³/g.

2. The absorbable topical hemostat according to claim 1, wherein the diameter of the fibers is 15 to 45 μm.

3. The absorbable topical hemostat according to claim 1, wherein the length of the fibers is 5 to 50 mm.

4. The absorbable topical hemostat according to claim 2, wherein the length of the fibers is 5 to 50 mm.

5. The absorbable topical hemostat according to claim 4, wherein the crosslinking is carried out at a temperature of 60° to 180° C.

6. The absorbable topical hemostat according to claim 4, wherein the crosslinking is carried out at a temperature of 95° to 150° C.

7. The absorbable topical hemostat according to claim 1, wherein the specific volume is 40 to 70 cm³/g.

8. The absorbable topical hemostat according to claim 4, wherein the specific volume is 40 to 70 cm³/g.

9. The absorbable topical hemostat according to claim 1, wherein the hemostat is made by contacting insoluble collagen obtained from the skin, bone, cartilage, tendon or an internal organ of a mammal with a protease to digest telopeptide and form a solution of solubilized atelocollagen, dissolving the solution in aqueous hydrochloric acid to obtain atelocollagen fibers, wet spinning the atelocollagen fibers with aqueous ammonium sulfate, desalting and dehydrating the spun atelocollagen fibers with methanol, drying and cutting the spun atelocollagen fibers to a desired length, air blowing the fibers and subjecting the fibers to a heat treatment at a temperature of 50° to 200° C.

* * * * *

UNITED STATES PATENT AND TRADEMARK OFFICE
CERTIFICATE OF CORRECTION

PATENT NO. : 5,679,372
DATED : October 21, 1997
INVENTOR(S) : Shimizu et al

It is certified that error appears in the above-identified patent and that said Letters Patent is hereby corrected as shown below:

On the title page, item [19], replace "Shimuzu et al." with --Shimizu et al.--.

Title Page, [75] Inventors: replace "Shimuzu, Uji" with --Shimizu, Kyoto--;

Signed and Sealed this

Twentieth Day of July, 1999

Attest:

Q. TODD DICKINSON

Attesting Officer

Acting Commissioner of Patents and Trademarks